(12) United States Patent
Morita (10) Patent No.: US 7,062,007 B2
(45) Date of Patent: Jun. 13, 2006

(54) TOMOGRAPHY DEVICE

(75) Inventor: Hisanori Morita, Kyoto (JP)

(73) Assignee: Shimadzu Corporation, Kyoto-Fu (JP)

( * ) Notice: Subject to any disclaimer, the term of this patent is extended or adjusted under 35 U.S.C. 154(b) by 0 days.

(21) Appl. No.: 10/857,750

(22) Filed: May 27, 2004

(65) Prior Publication Data

US 2005/0276374 A1 Dec. 15, 2005

(51) Int. Cl.
*A61B 6/00* (2006.01)

(52) U.S. Cl. .......................................... 378/17; 378/62

(58) Field of Classification Search .................. 378/4, 378/17, 20, 21, 62, 193, 195, 196, 197, 198, 378/205; 250/370.08, 370.09
See application file for complete search history.

(56) References Cited

U.S. PATENT DOCUMENTS 6,309,102 B1 * 10/2001 Stenfors ...................... 378/197
6,377,656 B1 * 4/2002 Ueki et al. .................. 378/98.7

FOREIGN PATENT DOCUMENTS

JP          2002-267622        9/2002

OTHER PUBLICATIONS

Patent Abstracts of Japan for JP2002-267622 published on Sep. 18, 2002.

* cited by examiner

*Primary Examiner*—Courtney Thomas
(74) *Attorney, Agent, or Firm*—Darby & Darby (57) ABSTRACT

A tomography device for imaging a body has a first imaging member, a second imaging member, and an imaging condition setting member for setting imaging conditions based on a superimposition of an effective tomographic image range and an image obtained using the second imaging member. The first imaging member includes a radiation source for radiating an electromagnetic wave at the body, a detecting member for detecting the electromagnetic wave radiated at and transmitted through the body, and a scanning member for applying scanning motion to the radiation source and the detecting member. The second imaging member obtains a body image from a direction different from a radiation direction from the radiation source to the detecting member used for imaging the body. The tomographic image range is determined based on a scanning range of the scanning member associated with the radiation source and the detecting member.

16 Claims, 10 Drawing Sheets

TOMOGRAPHY DEVICE

BACKGROUND OF THE INVENTION

The present invention relates to a tomography device used in medical fields and industrial fields such as nondestructive testing, RI (radio isotope) testing, and optical testing.

Examples of these types of devices include fluoroscope devices and C-arm fluoroscopic devices. These type of devices can, for example, be equipped with an X-ray detector in the form of an FPD (flat-panel detector) and an X-ray tube facing the detector. A worktop (bed) on which a detection body is mounted is raised and lowered or moved horizontally. A tomographic image of the detection body is obtained by performing a scan so that the X-ray detector and the X-ray tube are moved horizontally in opposite directions (e.g., see Japanese laid-open patent publication number 2002-267622 (page 4, FIG. 1, FIG. 2)).

The device of the above reference, however, has the following problems. When X-rays are radiated from the X-ray tube during the scanning operation, there is a cross section known as a focal plane. This focal plane provides the most effective X-ray field of view. The region for which a tomographic image can be reconstructed is broadest for this focal plane, and the region where this reconstruction can take place becomes narrower the further away one is from the focal plane. Thus, there can be cases where the detection body being observed falls outside the region within which image reconstruction is possible. Since the relationship between the bed height and the position of the focal plane is known, conventional tomographic imaging places the body within the region where reconstruction is possible by adjusting the bed-height factor of the imaging conditions. Stated another way, it is difficult to adjust imaging conditions for the reconstruction range in any way other than adjusting the bed height.

SUMMARY OF THE INVENTION

The object of the present invention is to overcome these problems and to provide a tomographic imaging device that allows imaging conditions to be easily set before tomographic imaging so that a body being observed is located within a reconstruction range.

As a result of extensive research to overcome the problems described above, the present inventor observed the following.

Figure 8:
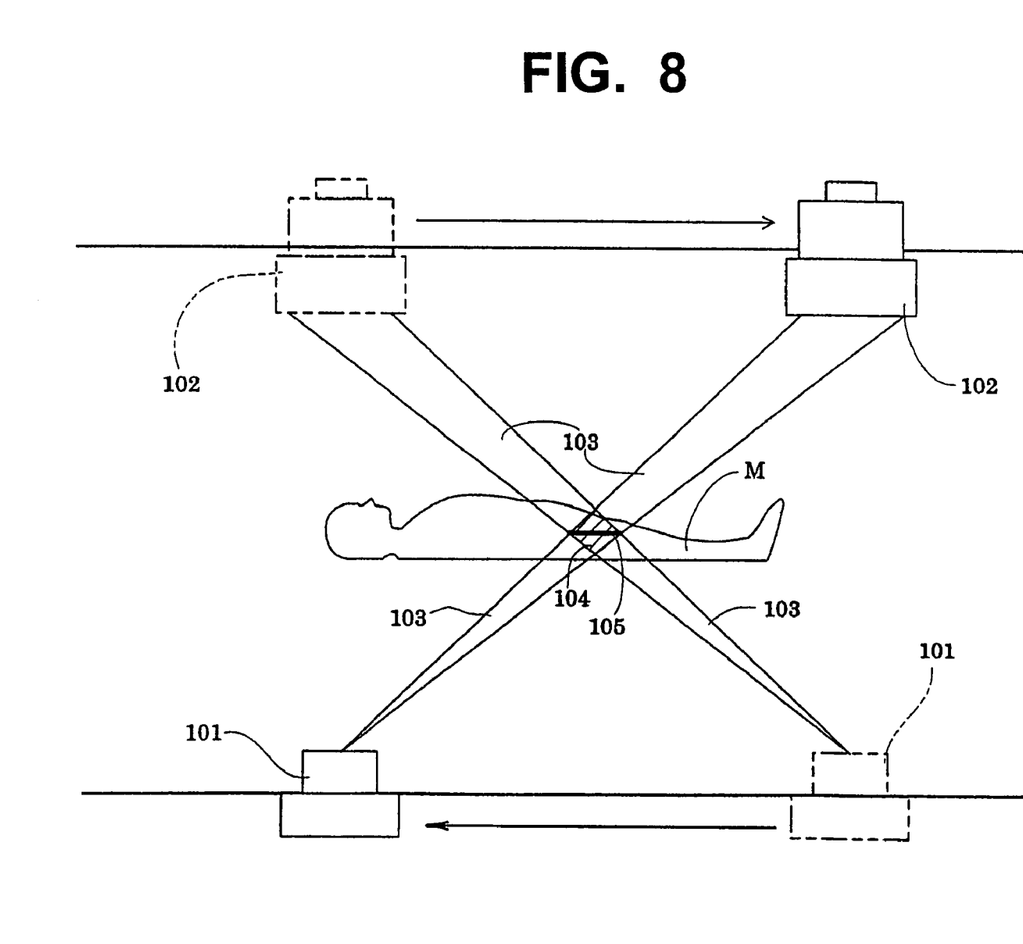
FIG. 8 is a simplified drawing illustrating tomographic imaging when an X-ray tube and an X-ray detector are interposed by a body and are scanned horizontally in opposite directions.

The present inventor concentrated on the reconstructable range described above. To simplify the description, FIG. 8 shows a radiation source, e.g., an X-ray tube 101, and detecting means, e.g., an X-ray detector 102 (such as an FPD or an image intensifier), moving horizontally in opposite directions interposed by a body M. FIG. 8 shows the scannable range (hereinafter this scannable range is referred to as "scan width") of the X-ray tube 101 and the X-ray detector 102 and the radiation ranges 103 wherein X-rays are radiated from the X-ray tube 101 to the X-ray detector 102 when the X-ray tubes 101 and the X-ray detector 102 are positioned at the ends of the scan width.

As shown in FIG. 8, an effective range 104 is formed as a four-sided shape by the superimposition of the radiation ranges 103 of the X-rays when the X-ray tube 101 and the X-ray detector 102 are positioned at the ends of the scan width. The plane within the effective range where the reconstructable range is largest is the focal plane 105 described above. The reconstructable range becomes smaller as the distance from the focal plane 105 increases. Thus, a region in the body M can be positioned within the reconstructable range by allowing the vertical position of the worktop (bed) on which the body M is mounted to be adjusted.

Figure 9:
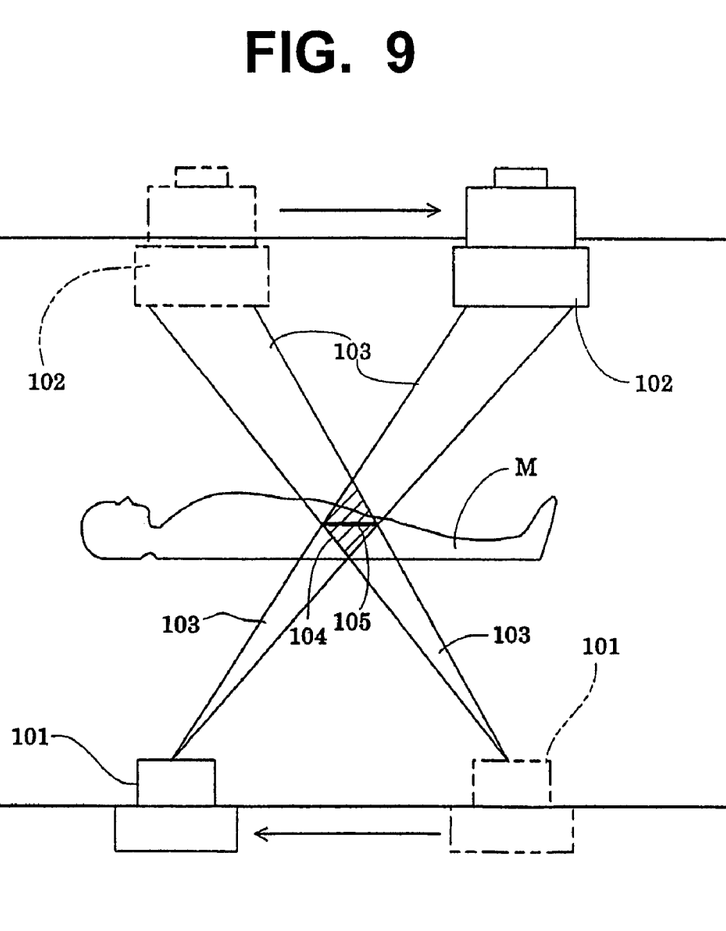
FIG. 9 is a simplified drawing illustrating tomographic imaging when the scan width setting of the X-ray tube and the X-ray detector is changed.
Figure 10:
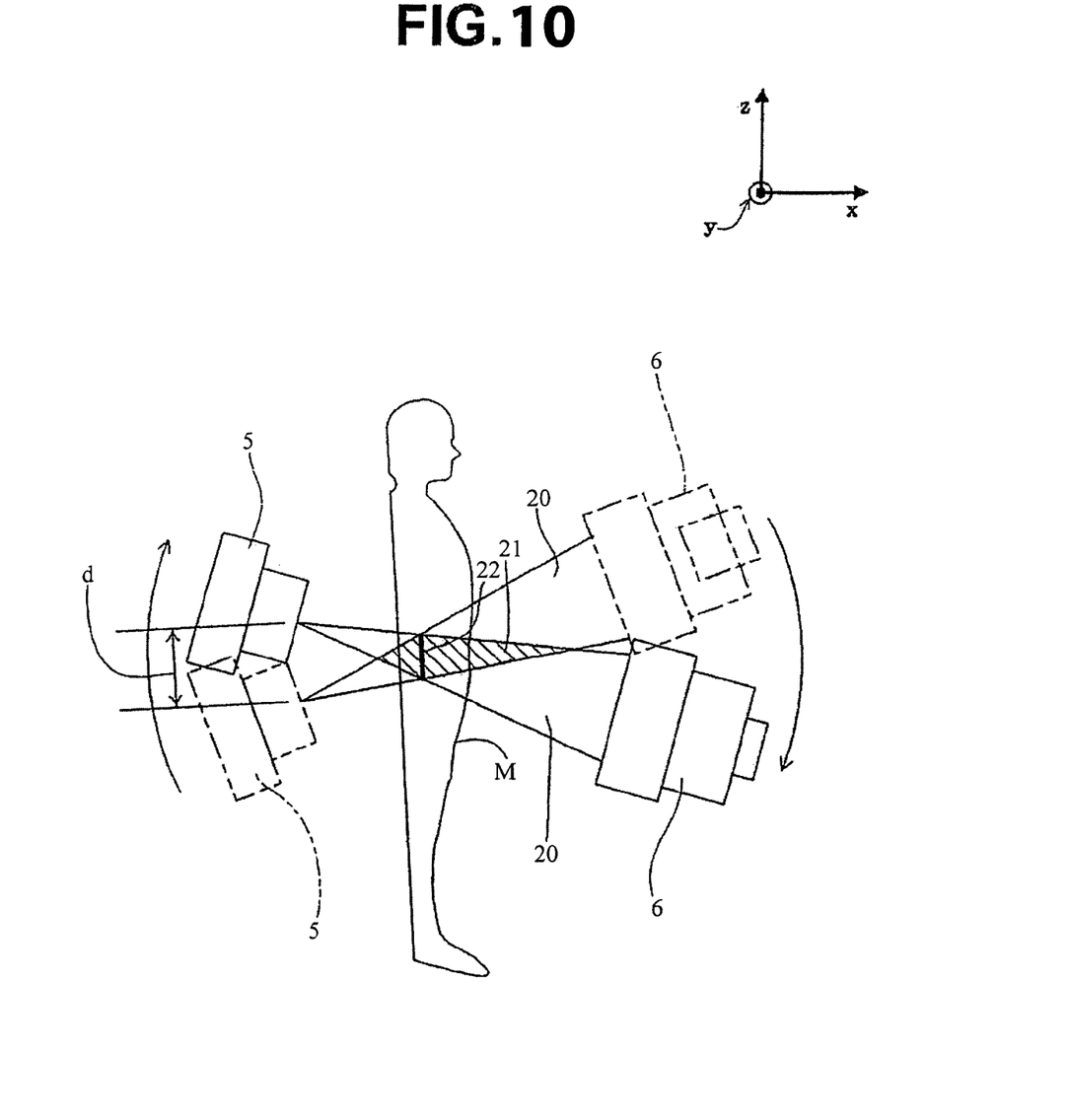
FIG. 10 is a simplified side-view drawing illustrating an effective range of a tomographic image and the scan preformed at an angle.

Similarly, as shown in FIG. 9, when the scan width of the X-ray tube 101 and the X-ray detector 102 is changed, the effective range 104 can be changed. By referring to the X-ray radiation range 103 and the effective range 104 in within the radiation range 103 shown in FIG. 8 and FIG. 9, imaging conditions other than bed vertical position can be set appropriately so that the region of the body to be observed can be positioned in the reconstructable range. Instead of determining the effective range 104 based on determining the X-ray radiation 103 through actual application of X-rays, it is possible to determine the effective range 104 from conditions such as the scan width of the X-ray tube 101 and the X-ray detector 102, i.e., from the geometry of the tomographic imaging devices such as the X-ray tube 101 and the X-ray detector 102.

Thus, there is no need to perform imaging of the X-ray radiation range 103. Instead, before imaging, the effective range 104 is determined ahead of time from the scan range, and imaging is performed so that the imaging results have the directions shown in FIG. 8 and FIG. 9. Then, the effective range 104 and the image of the body M can be superimposed as in FIG. 8 and FIG. 9, and this can be used to set up imaging conditions. The present invention is based on this idea and is described as follows.

An implementation of the invention provides a tomography device equipped with first imaging means performing tomographic imaging of a body wherein the first imaging means includes a radiation source radiating an electromagnetic wave at the body, detecting means detecting the electromagnetic wave radiated at and transmitted through the body, and scanning means scanning applying scanning motion to the radiation source and the detecting means. The tomography device includes: second imaging means imaging the body from a direction different from an illumination direction from the illumination source to the detecting means used for imaging the body; and imaging condition setting means setting imaging conditions based on superimposing an effective tomographic image range, determined based on a scanning range of the scanning means for the illumination source and the detecting means, and an imaging image obtained using the second imaging means.

According to the implementation, the radiation source radiates the body with electromagnetic waves. The radiated electromagnetic waves pass through the body and detecting means detects the transmitted electromagnetic waves while scanning means makes the radiation source and detecting means perform a scanning motion. As a result, first imaging means, equipped with the radiation source, detecting means, and scanning means, performs tomographic imaging of the body. This tomographic imaging of the body is performed after imaging condition setting means sets up imaging conditions. More specifically, in order to have imaging condition setting means set up imaging conditions, second imaging means images the body from a direction other than the radiation direction used by first imaging means extending from the radiation source to detecting means. Furthermore, the effective range of the tomographic image is determined from scanning means' scanning range for the radiation source and detecting means. This effective range and the image provided by second imaging means are superimposed, and imaging condition setting means sets up imaging conditions based on this superimposition. To summarize, before first imaging means performs tomographic imaging, second imaging means performs imaging. Then, imaging conditions are set up based on the effective range, which serves as a guide for the reconstructable range, and the tomographic image from second imaging means. Then first imaging means can perform tomographic imaging. As a result, before first tomographic imaging is performed by first imaging means, imaging conditions can be easily set up so that the region to be observed on the body can be positioned in the reconstructable range.

In this specification, the imaging of the body by second imaging means is referred to as "preliminary imaging," and the tomographic imaging performed by first imaging means after imaging conditions have been set up by imaging condition setting means is referred to as "main imaging".

The imaging condition can be a position of the body, and the imaging condition setting means sets the position of the body based on a relationship between the superimposed effective range and an imaging image obtained using the second imaging means.

The position of the body can be the horizontal position, the vertical position, or the like. Alternatively, the condition can be a scanning range of the scanning means for the illumination source and the detecting means position of the body, and the imaging condition setting means sets the scanning range for the radiation source and the detecting means based on a relationship between the superimposed effective range and an imaging image obtained using the second imaging means.

Furthermore, the condition can be a combination of then two conditions described in the above two paragraphs.

Alternatively, displaying means can be included displaying the superimposed effective range, the imaging image obtained using the second imaging means, the imaging condition set up by the imaging condition setting means, and a tomographic image obtained using the first imaging means with the imaging condition setting. Displaying means can be used to confirm whether tomographic imaging can be performed and can also be used to indicate the relationship between the effective range or the imaging conditions and the tomographic image. Alternatively, the imaging condition displayed on the displaying means can be a position of the body. Alternatively, a single imaging means can be used as both the first imaging means and the second imaging means.

This specification also discloses a method for performing tomographic imaging.

(1) The present invention provides a method for performing tomographic imaging of a body wherein a radiation source radiates the body with an electromagnetic wave, the radiated electromagnetic wave is transmitted through the body, detecting means detects the transmitted electronic wave, and scanning means scans the electromagnetic radiation source and detecting means. This method for performing tomographic imaging includes: (a) a step for determining an effective range for the tomographic image based on scanning means' scanning range for the radiation source and detecting means; (b) a step for preliminary imaging of the body from a direction different from the axis from the radiation source to detecting means; (c) a step for setting up imaging conditions based on superimposition of the effective range determined in the effective range determination step in (a) and the image obtained in the preliminary imaging step in (b); (d) a step for performing main imaging based on the imaging conditions set up in the imaging condition setting step in (c) by using scanning means to scan the radiation source and detecting means while the radiation source radiates electromagnetic waves and detecting means detects the electromagnetic waves.

According to the invention in (1), in the effective range determining step in (a), the effective range of the tomographic image is determined based on scanning means' scanning range for the radiation source and detecting means; and in the preliminary imaging step in (b), preliminary imaging of the body is performed from a direction different from the radiation direction from the radiation source to detecting means. As a result, the effective range of the tomographic image, which serves as a guide for the reconstructable range, can be determined in the effective range determining step in (a). This effective range and image obtained in the preliminary imaging step in (b) are superimposed, and the imaging condition setting step in (c) is able to set up imaging conditions based on this superimposition. Then, based on the imaging conditions set up in the imaging condition setting step in (c), the main imaging, i.e., tomographic imaging, can be performed by having scanning means scan the radiation source and detecting means while the radiation source radiates electromagnetic waves and detecting means detects these electromagnetic waves. In this manner, imaging conditions can be set up easily before tomographic imaging, i.e., the main imaging, is performed so that the region of the body to be observed can be positioned within the reconstructable range.

(2) In the tomographic imaging method in (1), the effective range determining step in (1), the preliminary imaging step in (b), and the imaging condition setting step in (c) are repeated multiple times until at least a portion of the region of the body to be observed is in the reconstructable range.

(3) In the tomographic imaging method described in (1) or (2), the imaging condition is the position of the body, and the imaging condition setting step in (c) superimposes the effective range determined in the effective range determining step in (a) and the image obtained in the preliminary imaging step in (b), with the position of the body being set up based on the relationship in this superimposition of the effective range and the image.

(4) In the tomographic method described in any one of (1) through (3), the imaging condition is scanning means' scanning range for the radiation source and detecting means, and the imaging condition setting step in (c) superimposes the effective range determined in the effective range determining step in (a) and the image obtained in the preliminary imaging step in (b), with the position of the body being set up based on the relationship in this superimposition of the effective range and the image.

Specific methods for performing tomographic imaging can be implemented according to the inventions in (2) through (4) above. Of course, the inventions in (2) through (4) can be combined as appropriate.

The above, and other objects, features and advantages of the present invention will become apparent from the following description read in conjunction with the accompanying drawings, in which like reference numerals designate the same elements.

BRIEF DESCRIPTION OF THE DRAWINGS

FIG. 6 shows one set of examples for displays on a monitor.

DETAILED DESCRIPTION OF THE PREFERRED EMBODIMENTS

An embodiment of the present invention will be described, with references to the drawings.

Figure 1:
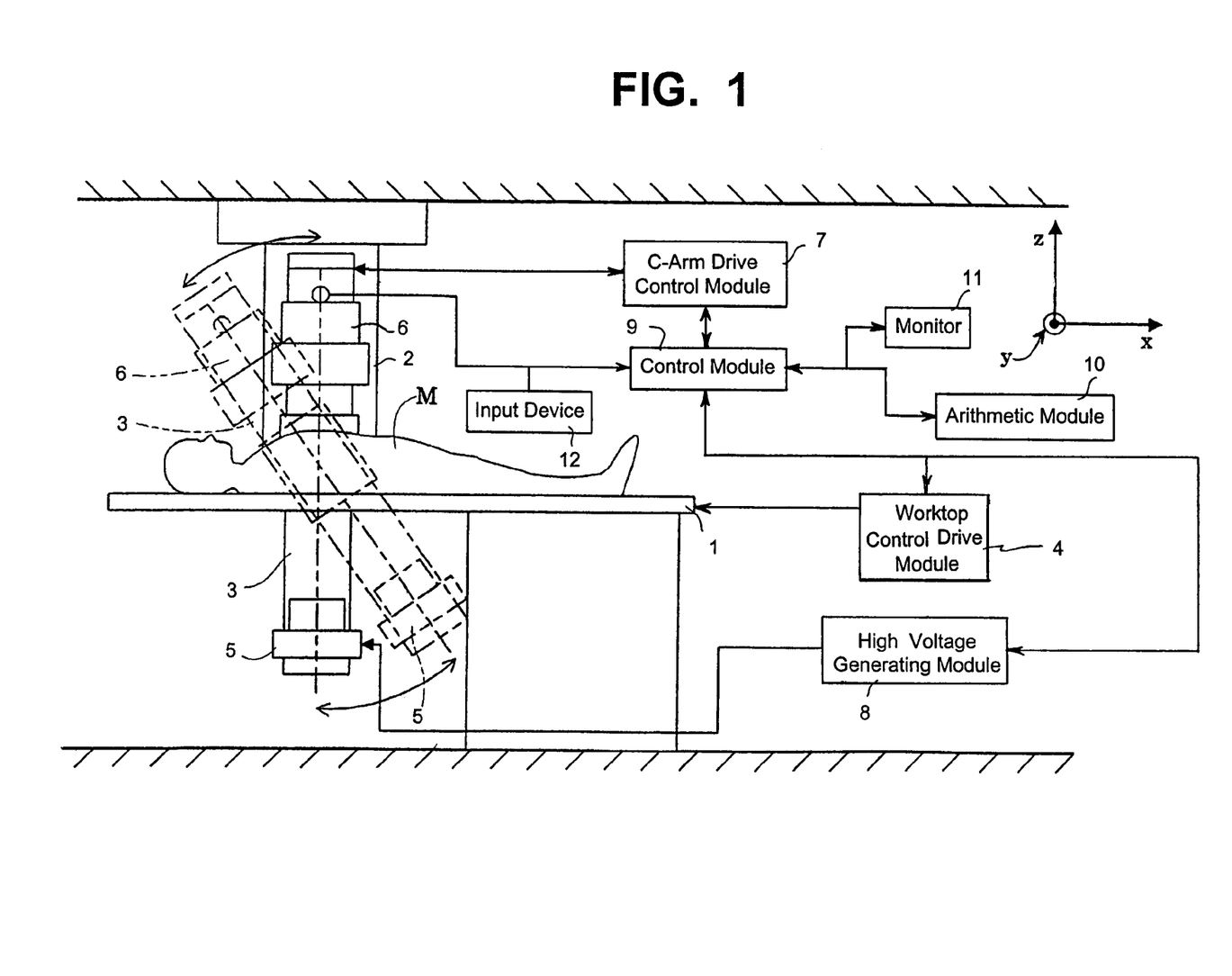
FIG. 1 is a simplified side-view drawing showing the structure of a tomography device according to this embodiment.
Figure 2:
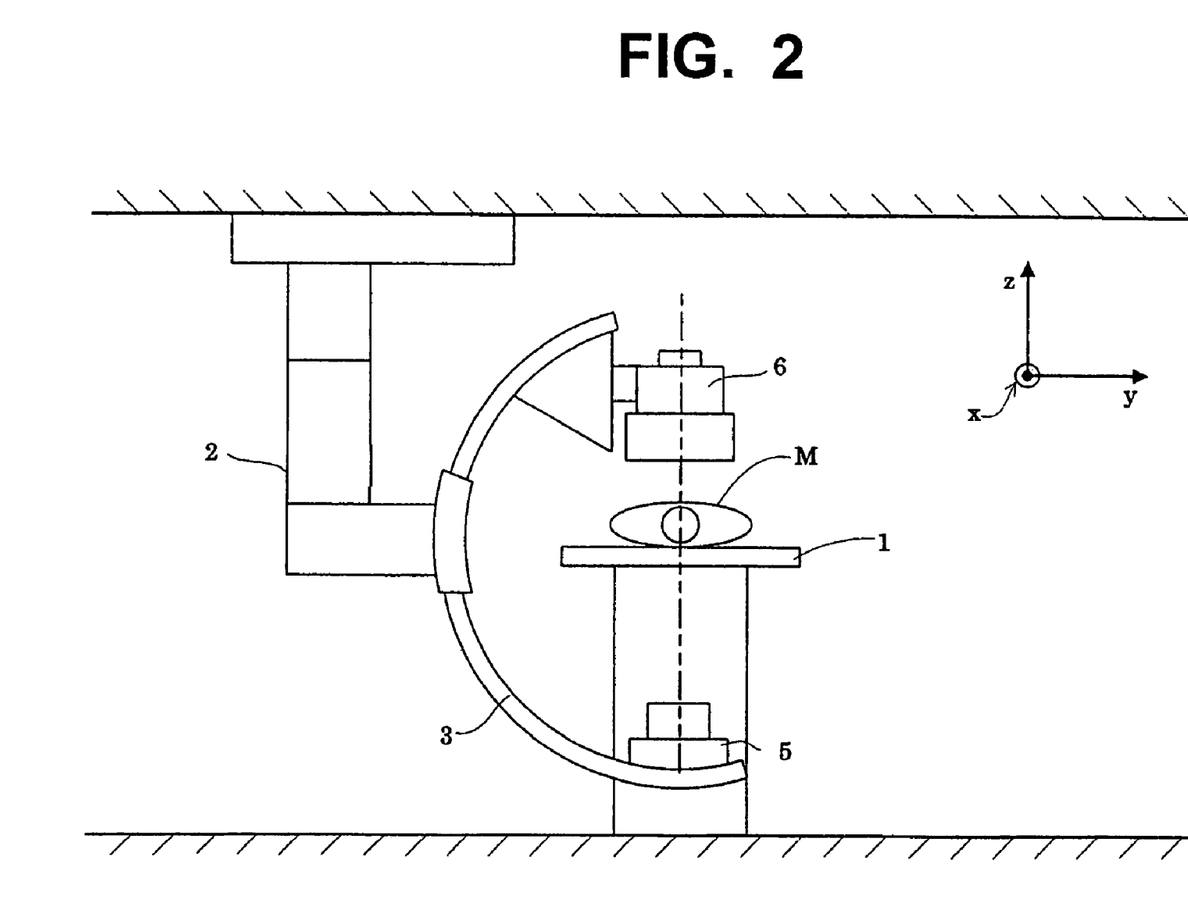
FIG. 2 is a simplified front-view drawing showing the structure of a tomography device according to this embodiment.
Figure 3:
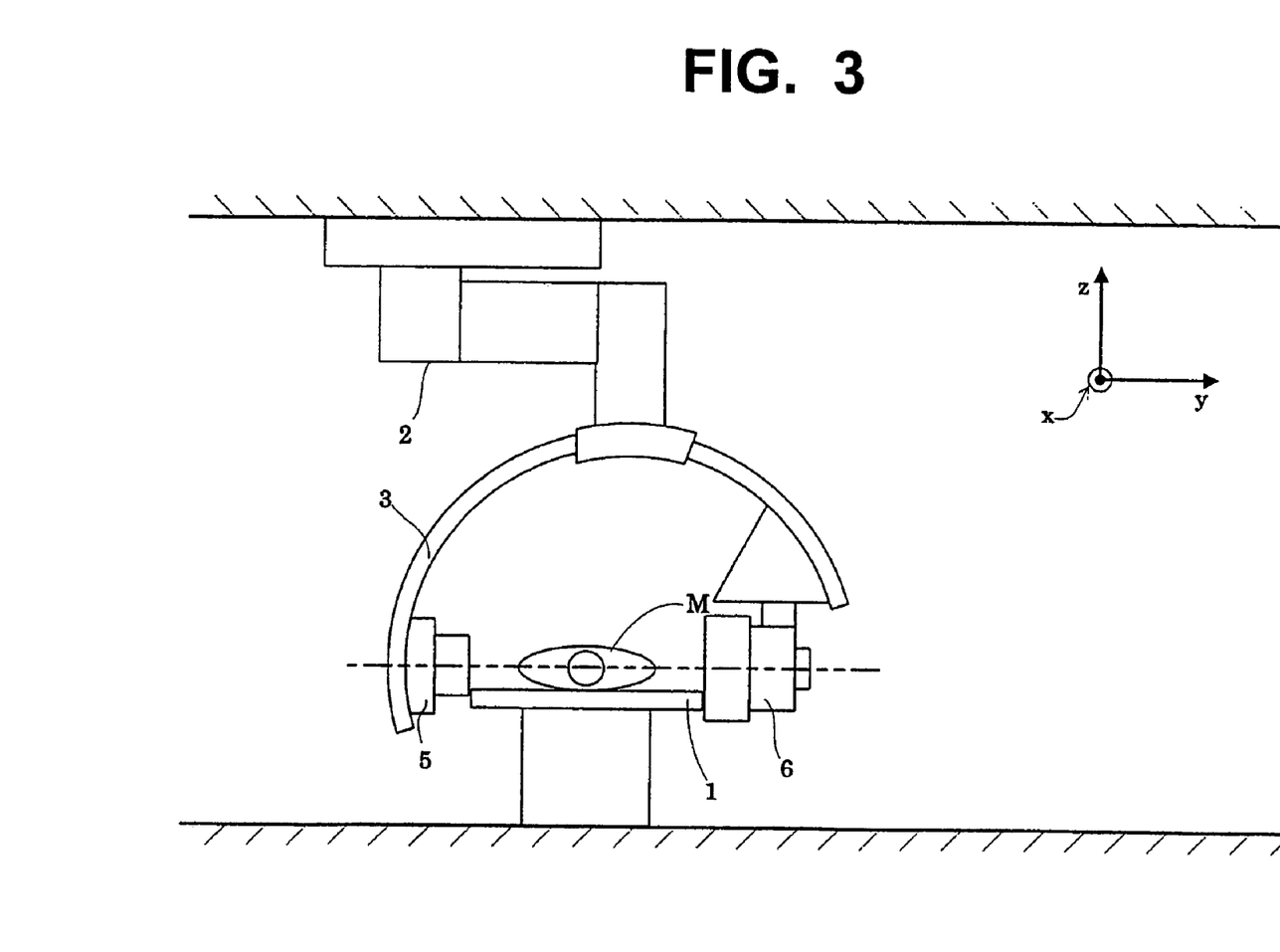
FIG. 3 is a front-view drawing of a tomography device during preliminary imaging.
Figure 4:
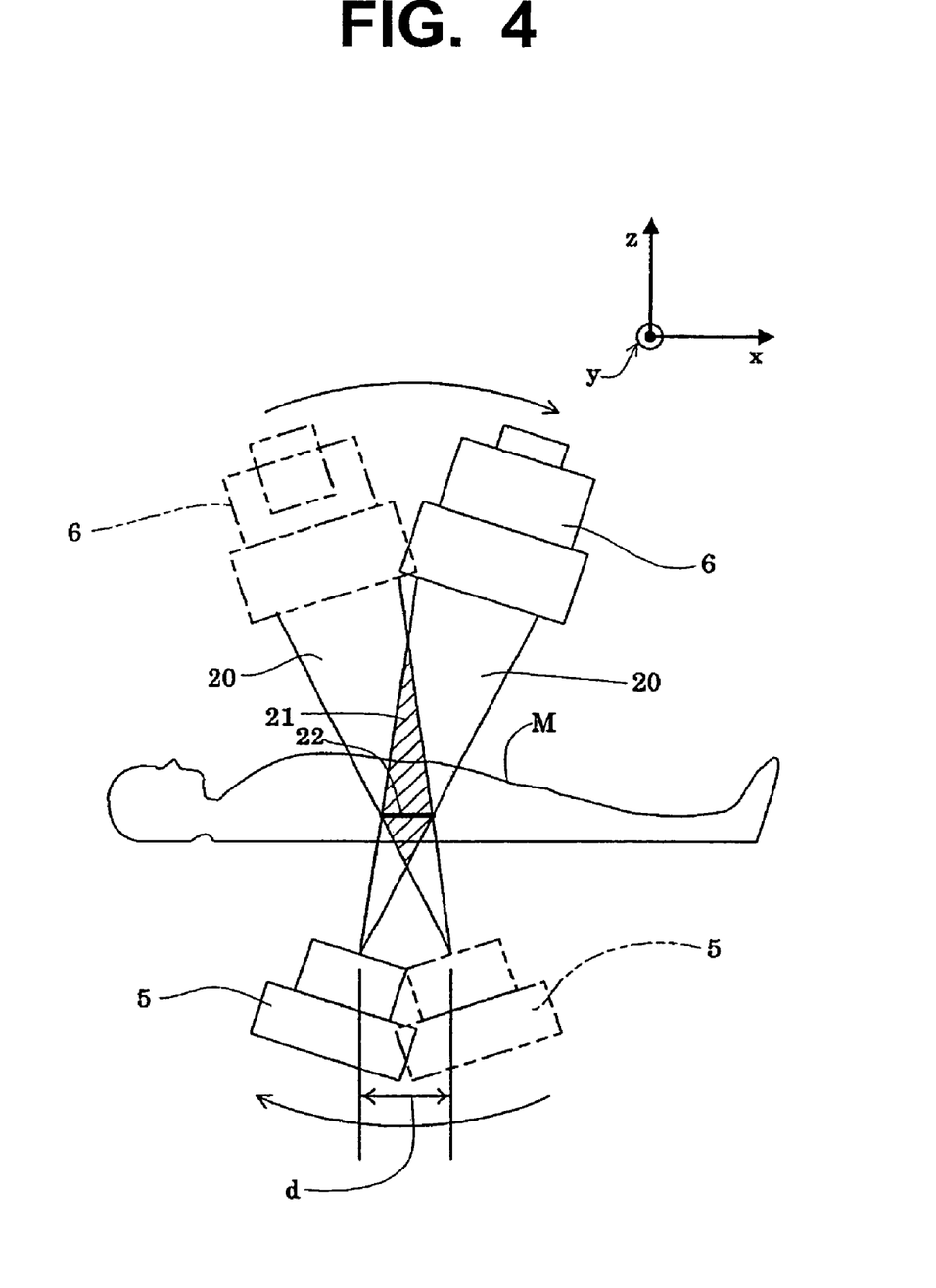
FIG. 4 is a simplified side-view drawing illustrating an effective range of a tomographic image.
Figure 5:
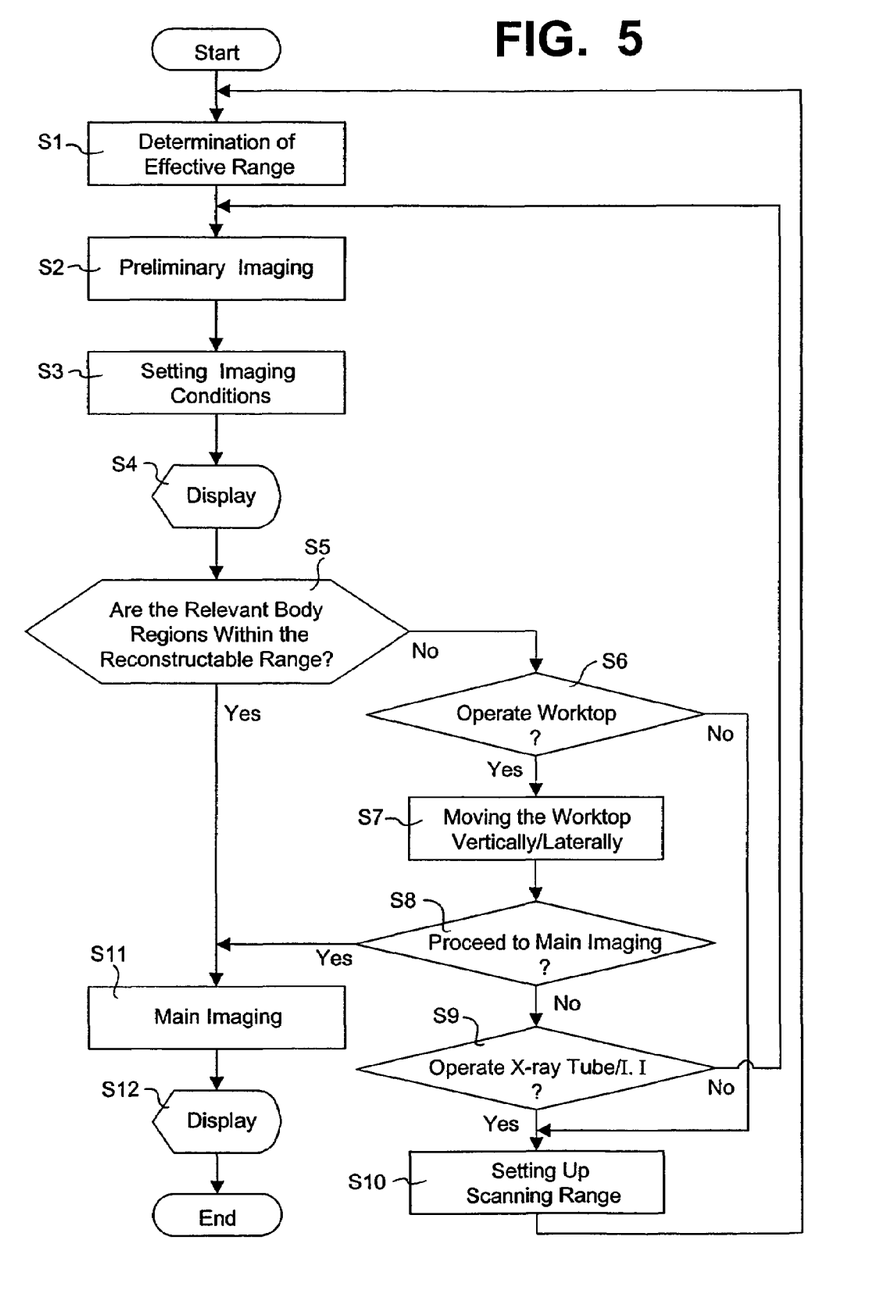
FIG. 5 is a flowchart showing a method for tomographic imaging.

FIG. 1 shows a side-view drawing of a tomographic device according to this embodiment. FIG. 2 shows a front view thereof. FIG. 3 is a front-view drawing of a tomographic imaging device during preliminary imaging. FIG. 4 is a side-view drawing that schematically shows the effective range of a tomographic image. FIG. 5 is a flowchart illustrating a tomographic imaging method. In this embodiment, a C-arm fluoroscopic device is used as an example of a tomographic imaging device, and an X-ray tube radiating X rays is used as an example of an illumination source.

As shown in FIG. 1 and FIG. 2, the device of this embodiment includes, broadly, a worktop 1 for mounting and inspecting an inspection body M, a support post 2; and a C-arm 3. This support post 2 is attached to the ceiling surface and is formed as a multi-jointed structure.

The worktop 1 can be raised and lowered and can also move along the body axis of the inspection body M or an axis perpendicular to the body axis extending along a horizontal plane. A worktop drive control module 4 controlling the driving of the worktop 1 is connected to the worktop 1, and this worktop drive control module 4 controls a drive mechanism driving the worktop 1, a brake mechanism stopping horizontal movement of the body axis of the worktop 1 or the like, a break release mechanism releasing horizontal movement along the body axis or the like, a detection mechanism detecting the position of the worktop 1, and the like (these elements are not shown in the figure).

An X-ray tube 5 radiating X-rays on to the inspection body M is supported at one end of the C-arm 3 and on the other end is supported an image intensifier (hereinafter abbreviated as "I.I") 6 detecting X-rays radiated on to the body M and converting this into an optical image. The C-arm 3 is formed so that it can rotate around the body axis of the body M (the x axis in FIG. 1 and FIG. 2) and an axis lying on a horizontal plane that is perpendicular to the body axis of the body M (the y axis in FIG. 1 and FIG. 2), The X-ray tube 5 corresponds to the illumination source of the present invention and the I.I 6 corresponds to detecting means of the present invention.

The C-arm drive control module 7, which controls the driving of the C-arm 3 and the support post 2, are connected to the support post 2 and the C-arm 3, respectively. The C-arm drive control module 7 controls the drive mechanisms driving the support post 2 and the C-arm 3 and the detection mechanisms detecting the positions of the support post 2 and the C-arm 3 (the drive mechanisms and the detection mechanisms are not shown in the figures). The support post 2 and the C-arm 3 correspond to scanning means in the present invention, and the support post 2 and the C-arm 3 and the X-ray tube 5 and the I.I 6 form first imaging means of the present invention. Also, a high voltage generating module 8 providing tube voltage and tube current to the X-ray tube 5 is connected to the X-ray tube 5.

Because the support post 2 is formed as a multi-jointed structure as described above, it is possible, for example, to image the body M by arranging the I.I 6 and the X-ray tube 5 supported by the C-arm 3 along the y axis in FIG. 3. Horizontal and vertical motion is applied to the worktop 1 so that the body M is placed in the imaging region. The imaging performed from the direction shown in FIG. 3 serves as a preliminary imaging described later. Thus, the support post 2, the C-arm 3, the X-ray tube 5, and the I.I 6 also correspond to second imaging means of the present invention. More specifically, in this embodiment, the support post 2, the C-arm 3, the X-ray tube 5, and the I.I6 serve as both first imaging means and second imaging means of the present invention.

The data converted into an optical image by the I.I 6 is sent by the control module 9 to an arithmetic module 10. After various arithmetic operations (e.g., reconstruction) are performed, a tomographic image is output. Geometry conditions of the device of this embodiment, i.e., the scanning range conditions of the X-ray tube 5 and the I.I 6 controlled for scanning by the support post 2 and the C-arm 3, are sent to the arithmetic module 10 and are converted to an effective range 21 (see FIG. 4) and a focal plane 22 (see FIG. 4) for the tomographic image. The imaging data of the body M obtained in the preliminary imaging is sent by the control module 9 to the arithmetic module 10 as data to be superimposed on the effective range 21 and the focal plane 22. It should be noted that this preliminary imaging data is not the tomographic image. The control module 9 is formed to provide overall control over the worktop drive control module 4, the C-arm drive control module 7, the high voltage generating module 8, and the like.

For example, the control module 9 controls the worktop 1 by way of the worktop drive control module 4 so that imaging condition settings can be made, e.g., settings for the vertical position and the lateral position of the worktop 1 and, through these worktop 1 settings, settings for the vertical position and lateral position of the body M. Also, the control module 9 can, by controlling the drive on the support post 2 and the C-arm 3 by way of the C-arm drive control module 7, set up imaging condition settings such as the scanning range of the X-ray tube 5 and the I.I 6 and, through these X-ray tube 5 and I.I 6 settings, settings for an scan width d of the I.I 6 (see FIG. 4). In other words, the control module 9 can set up imaging conditions as well as performing overall control operations as described above, and the control module 9 and the worktop drive control module 4 and the C-arm drive control module 7 correspond to the imaging condition setting means of the present invention.

The data resulting from the various arithmetic operations performed by the arithmetic module 10, e.g., the tomographic image, the effective range 21 (see FIG. 4), and the like, are displayed on a monitor 11 by the control module 9. In addition to tomographic images and the effective range 21, the control module 9 can also display the imaging conditions described above on the monitor 11. The monitor 11 corresponds to displaying means of the present invention.

In addition, there is provided an input device 12, e.g., a keyboard or a mouse, and the operator uses the input device 12 to enter commands (instructions) for providing overall control over the elements connected to the control module 9 (e.g., the worktop drive control module 4, the C-arm drive control module 7, the high voltage generating module 8).

When the C-arm 3 rotates around the axis that lies on a horizontal plane and that is perpendicular to the body axis of the body M (the y axis in FIG. 1 and FIG. 2), the X-ray tube 5 and the I.I 6 supported at the ends of the C-arm become sloped relative to the perpendicular axis (the z axis in FIG. 1 and FIG. 2). When the C-arm 3 rotates around the y axis, the scannable range of the X-ray tube 5 and the I.I 6 is, as shown in FIG. 4, the scan width d. FIG. 4 shows an X-ray illumination range 20 radiated from the X-ray tube 5 to the I.I 6 when the X-ray tube 5 and the I.I 6 are positioned at the ends of the scan width d.

As shown in FIG. 4, the superimposition of the illumination ranges 20 when the X-ray tube 5 and the I.I 6 are positioned at the ends of the scan range d forms a rectangle, and this superimposed rectangle becomes the effective range 21 for the tomographic image. More specifically, within this effective range 21, X-rays are always radiated while the X-ray tube 5 and the I.I 6 are rotated in the scanning range within the scan width d. Thus, the region within the effective range 21 is the region in which an image can be reconstructed. The plane of the effective range 21 where this region that can be reconstructed is larges is the focal plane 22. The region that can be reconstructed becomes smaller when the distance from the focal plane 22 is greater. In the preliminary imaging, the body M in FIG. 4 is imaged from the direction shown in FIG. 3. The focal plane 22 and the effective range 21 formed by superimposition of the illumination ranges 20 are not data obtained from actual imaging but are determined before imaging based on the scanning ranges of the X-ray tube 5 and the I.I 6 as described above.

Next, the flowchart in FIG. 5 will be used to describe a tomographic imaging method.

(Step S1) Determination of Effective Range

The body M is mounted on the worktop 1. In order to move the worktop 1 to a predetermined vertical position and lateral position, the operator uses the input device 12 to enter commands to set the positions to the predetermined positions. The control module 9 and the worktop drive control module 4 moves the worktop 1 horizontally and vertically. The position for the body M is set by moving the worktop 1 to the predetermined vertical position and lateral positions.

In order to have the X-ray tube 5 and the I.I 6 operate according to the predetermined scan width d, the operator uses the input device 12 to enter commands to set up the predetermined scan width. The control module 9 and the arm drive control module 7 controls the support post 2 and the C-arm 3 and the like. Since the scanning range settings such as the scan width d are set up at this point, this scanning range is used to determine the effective range 21 and the focal plane 22 as shown in FIG. 4. This step S1 corresponds to the effective range determination step in (a) of the present invention.

(Step S2) Preliminary Imaging

Once the body M has been set up at a predetermined position and the X-ray tube 5 and the I.I 6 have been set up for a predetermined scan width d, preliminary imaging is performed from the direction shown in FIG. 3. Specifically, the X-ray tube 5 radiates X-rays and the I.I 6 detects these X-rays. This step S2 corresponds to the preliminary imaging step in (b) of the present invention.

In this embodiment, during the main imaging described later (step S11), if the C-arm 3 rotates around the axis on a horizontal plane and perpendicular to the body axis of the body M (the y axis in FIG. 1 and FIG. 2), the direction of the radiation (the direction of the scan path plane) from the X-ray tube 5 to the I.I 6 is aligned with the direction of the zx plane in FIG. 4 (the plane of the effective range 21) and the imaging direction for the body M is along the y axis in the preliminary imaging. However, if, during the main imaging, the C-arm 3 rotates around the body axis of the body M (the x axis in FIG. 1 and FIG. 2), the direction of the radiation in the main imaging from the X-ray tube 5 to the I.I 6 (the direction of the scan path plane) is aligned with the yz plane, which is the effective range plane, and the direction used for imaging the body M in the preliminary imaging can be, for example, along the x axis. Of course, the present invention is not restricted to the x axis perpendicular to the yz plane (scan path plane), and it would be possible to perform preliminary imaging from an oblique direction. Also, when the radiation direction (the direction of the scan path plane) from the X-ray tube 5 to the I.I 6 is in the zx plane, as in this embodiment, the present invention is not restricted to imaging along the y axis perpendicular to the ax plane, and preliminary imaging can be performed from an oblique direction. However, in terms of ease of confirmation of the reconstructable range, it would be preferable to image the body M from a direction perpendicular to the scan path plane during the preliminary imaging.

(Step S3) Setting Imaging Conditions

When the preliminary imaging in step S2 is completed, the imaging data of the body M obtained from the preliminary imaging and the effective range 21 determined at step S1 are superimposed. Using the superimposed effective range 21 and the imaging data from the preliminary imaging, settings are made by way of the worktop drive control module 4 or the C-arm drive control module 7 for the imaging conditions, e.g., the lateral position and vertical position of the body M, the scan width d of the X-ray tube 5 and the I.I 6, or the like. This step 3 corresponds to the imaging conditions setting step in (c) of the present invention.

(Step S4) Display

The operator decides whether to use the imaging conditions directly or to modify the imaging conditions. Thus, the operator confirms whether or not tomographic imaging can be performed with the initial tomographic imaging condition settings by looking at the monitor 11 and, based on the displayed results, decides either to use these imaging conditions directly or to modify the imaging conditions.

Figure 6A:
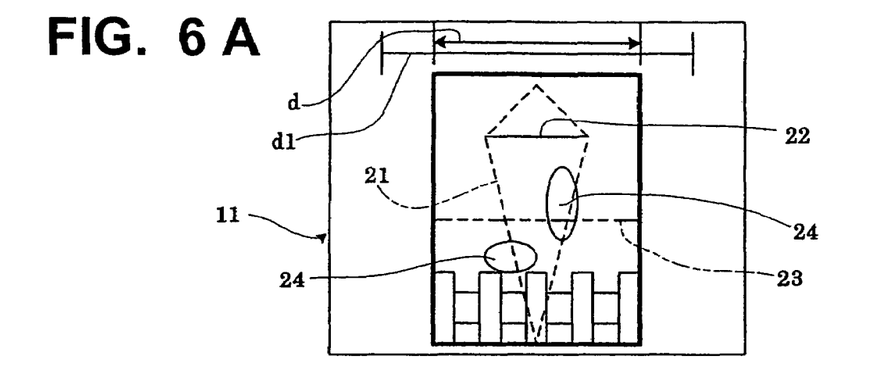
FIG. 6(a) shows the display of an effective range determined from the initial imaging condition setting and the superimposition obtained at steps S1, S2.
Figure 6B:
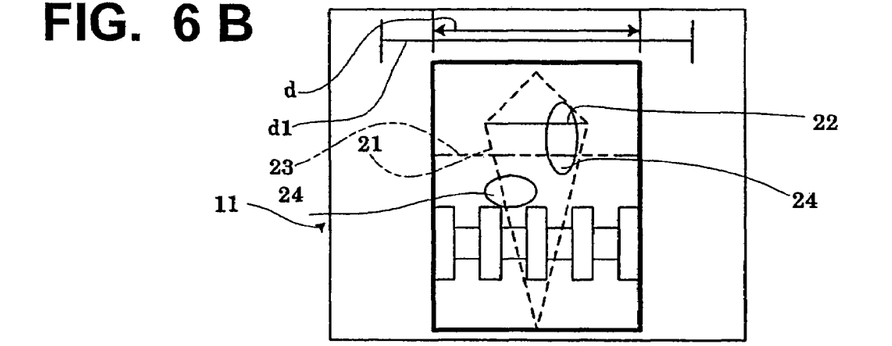
FIG. 6(b) shows the display of the imaging condition, the effective range, and the image data when the vertical position of the body is changed.
Figure 6C:
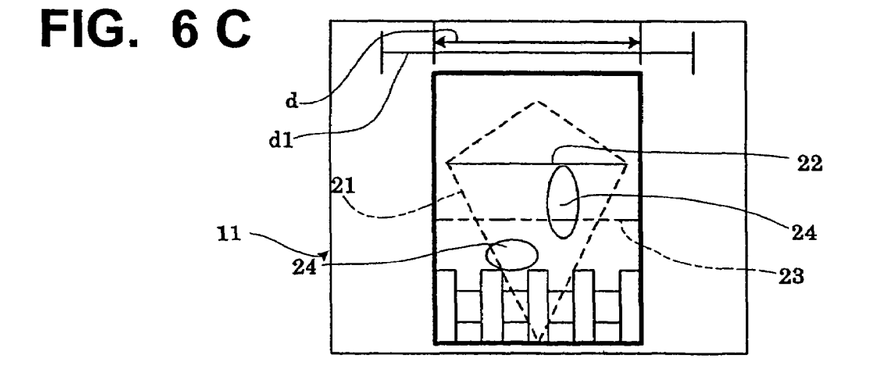
FIG. 6(c) shows the display of the imaging condition, the effective range, and the imaging data when the scan width is changed.

More specifically, the superimposed effective range 21 and the imaging data from the preliminary imaging is displayed along with the imaging conditions set up in step S1 are displayed on the monitor 11 by way of the arithmetic module 10 and the control module 9. An example of what is displayed on the monitor 11 is shown in FIG. 6. FIG. 6(*a*) shows how the initial imaging condition settings and the superimposed effective range 21 and imaging data obtained at step S1 and step S2 are displayed. FIG. 6(b) shows how imaging condition settings and the superimposed effective range 21 and imaging data are displayed when the vertical position of the body M is changed. FIG. 6(c) shows how imaging condition settings and the superimposed effective range 21 and imaging data are displayed when the scan width d is changed. At step S4, the display format shown in FIG. 6 (a) is displayed.

In FIG. 6, the imaging conditions are shown on the monitor 11 by displaying the vertical position of the worktop 1 and the lateral position, i.e., the vertical position and lateral position of the body M mounted on the worktop 1, and by displaying a tomography plane 23 parallel to the focal plane 22 and serving as a guide for the vertical position of the body M. The two elliptical regions in FIG. 6 are the regions 24 that are to be observed (these regions will be hereinafter referred to as relevant regions). Also, as shown in FIG. 6, imaging conditions other than the vertical position and lateral position of the body M can be shown by displaying the scan width d and the maximum scan width d.

(Step S5) Are the Relevant Body Regions within the Reconstructable Range?

Based on the display in FIG. 6(a), the operator decides whether or not the regions 24 to be observed, i.e., the relevant regions 24, lie within the reconstructable range. In the case of FIG. 6(a), not all of the relevant regions 24 on the tomography plane 23 are within the effective range 21, i.e., while they are not within the reconstructable range, the relevant regions 24 at the tomography plane are partially within the reconstructable range. Based on the display in FIG. 6(a), the operator uses the input device 12 to enter commands that determine whether to use the imaging conditions set up in the preliminary imaging directly or to change the imaging conditions so that more of the relevant regions 24 will be within the reconstructable range. If the imaging condition settings are to be used directly, control jumps to step S1. If the imaging conditions are to be changed, control proceeds to the following step S6.

(Step S6) Operate Worktop?

The operator decides whether or not to operate the worktop 1 to set the vertical position and lateral position of the body 1. The operator enters commands using the input device 12 to make this decision. If the operator decides to operate the worktop 1, control proceeds to the following step S7. If the worktop 1 is not to be operated, control proceeds to the scan range set-up operation at step S10 since, in this embodiment, the only possible imaging condition setting other than the positioning of the body M is the scannable range for the X-ray tube 5 and the I.I 6, i.e., setting the scan width d of the X-ray tube 5 and the I.I 6.

(Step S7) Moving the Worktop Vertically/Laterally

The worktop 1 is moved vertically/laterally by way of the control module 9 and the worktop drive control module 4. If the worktop 1 is to only be raised, the display changes via step S4 from what is shown in FIG. 6(a) to, for example, what is shown in FIG. 6(b). Raising the worktop 1 raises the vertical position of the body M, causing the tomography plane 23 and the relevant regions 24 to be raised.

(Step S8) Proceed to Main Imaging?

If the worktop 1 is moved vertically/laterally, it is possible to know roughly what will be displayed on the monitor 11 after the imaging conditions are changed by moving the worktop 1 vertically/laterally without repeating the determination of the effective range 21 at step S1, performing preliminary imaging at step S2, and providing a display on the monitor 11 at step S4. Thus, in this embodiment the operator can proceed to the main imaging operation or decide to repeat the preliminary imaging operation and the like. If the operator decides to proceed to the main imaging, control proceeds to the main imaging operation at step S11. If the preliminary imaging and the like is to be repeated, control proceeds to the following step S9.

(Step S9) Operate X-Ray Tube/I. I?

In addition to the moving of the worktop 1 vertically/laterally, at step S7 the operator can decide whether to operate the X-ray tube 5 and the I. I 6. If the X-ray tube 5 and the I. I 6 are to be operated, control jumps to the scanning range setup operation at step S10. Otherwise, control returns to the preliminary imaging operation at step S2.

(Step S10) Setting Up Scanning Range

The setting for the scannable region for the X-ray tube 5 and the I. I 6 is changed and the scan width d is changed via the control module 9 and the C-arm drive control module 7. If, for example, the scan width d is to be changed to an scan width d1, the display can change from what is shown in FIG. 6(a) to what is shown in FIG. 6(c) by way of step S4. Since the effective range 21 is changed when the scan width d is changed, control proceeds to step S1 so that the effective range 21 can be determined again.

(Step S11) Main Imaging

Based on the imaging conditions set up as described above, main imaging is performed, i.e., the control modules such as the control module 9, the worktop drive control module 4, the C-arm drive control module 7 perform tomographic imaging based on the new imaging settings and the X-ray radiation range 20. More specifically, the X-ray tube 5 radiates X-rays, which are detected by the I. I 6, and the X-ray tube 5 and the I. I 6 are operated by the support post 2 and the C-arm 3 so that they perform a scanning operation. This step S11 corresponds to the main imaging step in (d) in the present invention.

(Step S12) Display

Figure 7:
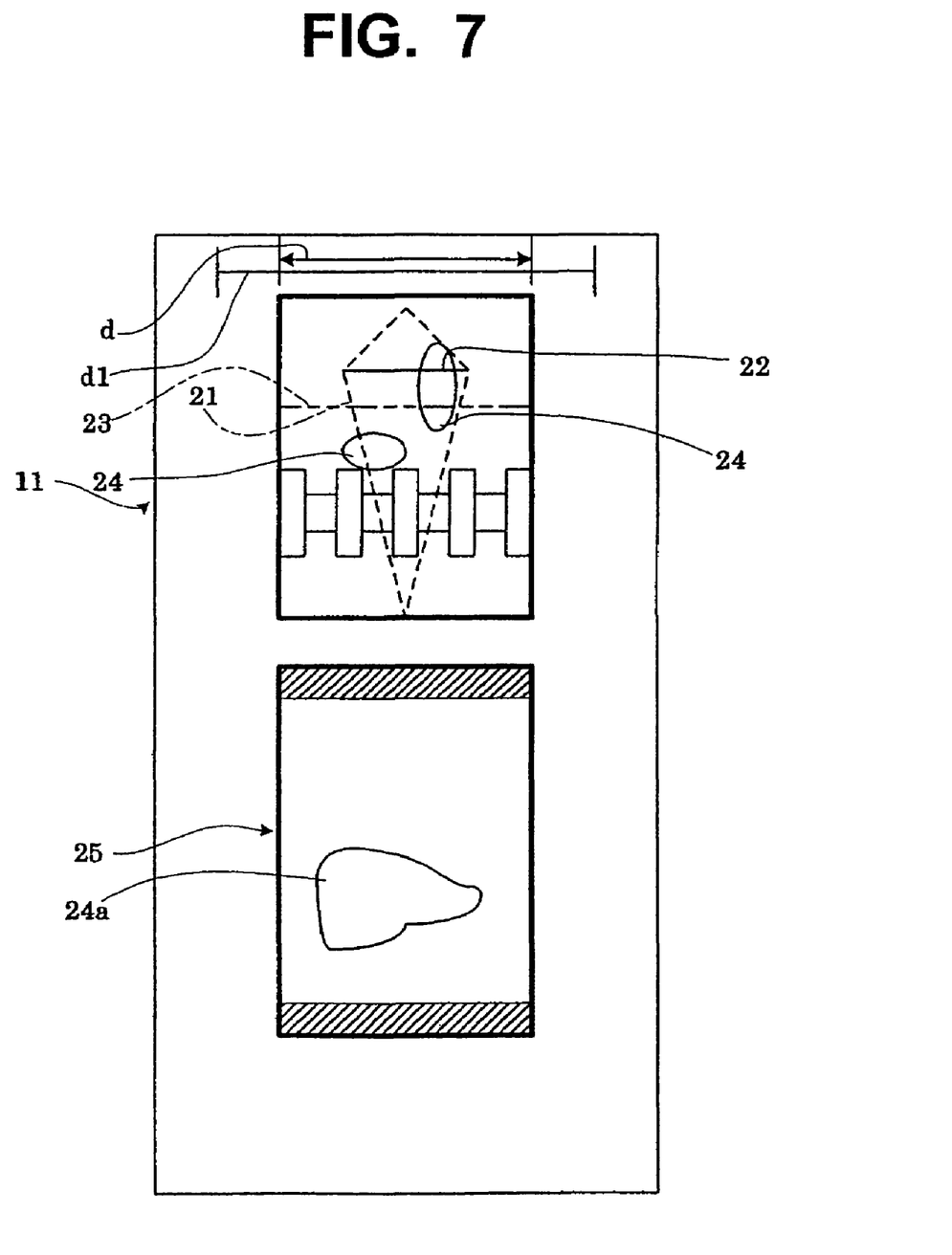
FIG. 7 shows the display when the vertical position of the body is changed and, in addition to the imaging condition and the effective range, the tomographic image is displayed below the imaging condition.

When the main imaging based on the imaging conditions is completed, the monitor 11 displays, in addition to the imaging conditions and the effective range 21 shown in the monitor 11 in FIG. 6, a tomographic image obtained through a reconstruction by the arithmetic module 10 using data from an optical image converted by the I. I 6. FIG. 7 shows an example of a display on the monitor 11 with the positioning information and the tomographic image. FIG. 7 shows a display in which the imaging conditions and the effective range 21 when the vertical position of the body M is changed as in FIG. 6(b). The tomographic image is displayed below these imaging conditions. In FIG. 7, there is shown a tomographic image 25 and an image 24a within the tomographic image 25 that is the image of the region 24 of the body to be observed on the tomographic plane 23, i.e., the relevant region 24 of the body to be observed on the tomographic plane 23.

In the tomographic imaging method according to step S1 through step S12 described above and the device of this embodiment, the effective range 21 of the tomographic image is determined based on the scanning range, e.g., the scan width d of the X-ray tube 5 and the I. I 6. In Step S2, in order to perform imaging from the direction shown in FIG. 3, the X-ray tube 5 radiates X-rays to the body M. These X-rays pass through the body M and the transmitted X-rays are detected by the I. I 6 to provide preliminary imaging. Step S1 provides the effective range 21 for the tomographic image which serves as a guide for the reconstructable range. By superimposing this effective range 21 and the image data of the body M obtained from the preliminary imaging in step S2, imaging condition settings based on this superimposition can be made. Based on the imaging condition settings that are made, main imaging, i.e., tomographic imaging, can be performed by using the support post 2 and the C-arm 3 to scan the X-ray tube 5 and the I. I 6. Before the tomographic imaging, i.e., the main imaging, the imaging conditions can be easily set up so that the region 24 of the body to be observed, i.e., the relevant region 24, can be located within the reconstructable range.

Also, this embodiment includes the monitor 11 to display the tomographic image 25, the superimposed effective range 21 and the imaging data, and imaging conditions. This makes it possible to see if the tomographic imaging was successful by looking at the monitor 11, and the monitor 11 can show the relationship between the tomographic image 25 and the effective range 21 or the imaging conditions.

Furthermore, with this method, the relationship between the effective range of the tomographic image and the imaging data is made clear by performing a preliminary imaging just once. Thus, there is no need as in the conventional technology to radiate X-rays while scanning in order to obtain a radiation range 20 used to determine the effective range 21. This has the advantage of reducing exposure for the body M. Also, in this embodiment, preliminary imaging is performed only once but it would also be possible to perform it multiple times. The data from these imagings could then be merged and superimposed on the effective range 21.

There are no special restrictions regarding the sequence in which the effective range 21 and the data from the imaging of the body M in the preliminary imaging are displayed on the monitor 11. The effective range 21 can be displayed after displaying the imaging data, or the imaging data can be displayed after the effective range 21 is displayed.

The present invention is not restricted to the embodiment described above. The following modifications may be made.

(1) In the embodiment described above, radiation, e.g., X-rays, is detected and a tomographic image is obtained from the radiation. However, other types of electromagnetic waves may be used. For example, light can be detected and a tomographic image can be obtained from the light.

(2) In the embodiment described above, an image identifier (I. I) is used as detecting means, but any means for detecting electromagnetic waves can be used. For example, an FPD (flat panel detector) can be used as detecting means.

(3) In the embodiment described above, the X-ray tube 5 radiating X-rays is used as the radiation source, but any means for radiating electromagnetic waves can be used. For example, the radiation source can be means for radiating light.

(4) In the embodiment described above, the worktop 1 on which the body M is mounted in a horizontal surface (the xy plane in FIG. 1) and the body M lies prone. However, the worktop 1 can be vertical (the yz plane or the zx plane) and the body M can be standing when performing tomographic imaging. Alternatively, the worktop 1 may be at an angle when performing tomographic imaging.

(5) In the embodiment described above, if the operator decides to put more of the relevant region 24 in the reconstructable range, the operator performs preliminary imaging, radiation range imaging, and the setting of imaging conditions (step S1 through step S10) repeatedly until the relevant region 24 is in the reconstructable range. However, it would be possible to have the preliminary imaging, radiation range imaging, and the setting of imaging conditions performed multiple times automatically until a predetermined proportion or all of the relevant region is in the reconstructable range. Of course, the steps for preliminary imaging, radiation range imaging, and the setting of imaging conditions can be performed just once before proceeding to the main imaging.

(6) In the embodiment described above, the example that is presented as the tomographic imaging device is a C-arm fluoroscopic device, i.e., a "non-CT (computed tomography)" imaging device. However, a CT-type cone-beam CT device can be used. There are no special restrictions as long as the device is a standard tomographic imaging device. The present invention is, of course, useful with non-CT devices.

With non-C-arm fluoroscopic devices, if, as shown in FIG. 8, the X-ray tube 101 and the X-ray detector 102 are to be scanned horizontally in opposite directions while interposed by the body M, the preliminary imaging can be performed from the axis perpendicular to the page in FIG. 8. Also, the present invention can be used for devices wherein the body is lying horizontally, the radiation axis connecting the X-ray tube 5 and the I. I6 is tilted at a predetermined angle relative to the plumb axis and rotational scanning around the plumb axis is performed to provide precession.

(7) In the embodiment described above, a single imaging means serves as first imaging means and second imaging means, but separate imaging means can also be used.

As the description above shows, second imaging means performs imaging of a body from a direction other than the imaging of first imaging means along the axis of the radiation direction from the radiation source to detecting means. The effective range for tomographic imaging, determined based on the scanning range of scanning means for the illumination source and detecting means, is superimposed on the image obtained by second imaging means to allow imaging condition setting means to set up imaging conditions. Thus, the effective range, which serves as a guide for the reconstructable range, and the image from the imaging can be used to set up the imaging conditions, after which first imaging means can perform tomographic imaging. As a result, before tomographic imaging is performed using first imaging means, imaging conditions can be set up easily so that the region of the body to be observed can be located in the reconstructable range.

Having described preferred embodiments of the invention with reference to the accompanying drawings, it is to be understood that the invention is not limited to those precise embodiments, and that various changes and modifications may be effected therein by one skilled in the art without departing from the scope or spirit of the invention as defined in the appended claims.

What is claimed is:

1. A tomography device comprising:
  first imaging means for performing tomographic imaging of a body, wherein said first imaging means includes a radiation source for radiating an electromagnetic wave at said body, detecting means for detecting said electromagnetic wave radiated at and transmitted through said body, and scanning means for applying scanning motion to said radiation source and said detecting means;
  second imaging means for imaging said body from a direction different from a radiation direction from said radiation source to said detecting means used for imaging said body; and
  imaging condition setting means for setting imaging conditions based on a superimposition of an effective tomographic image range and an image obtained using said second imaging means, said tomographic image range determined based on a scanning range of said scanning means associated with said radiation source and said detecting means.

2. A tomography device according to claim 1 wherein said condition is a position of said body, and said imaging condition setting means sets said position of said body based on a relationship between said superimposed effective range and the image obtained using said second imaging means.

3. A tomography device according to claim 1 wherein said condition is a scanning range of said scanning means for said radiation source and said detecting means position of said body, and said imaging condition setting means sets said scanning range for said radiation source and said detecting means based on a relationship between said superimposed effective range and the image obtained using said second imaging means.

4. A tomography device according to claim 1 further comprising:
    displaying means for displaying said superimposed effective range, said image obtained using said second imaging means, said imaging condition set up by said imaging condition setting means, and a tomographic image obtained using said first imaging means with said imaging condition setting.

5. A tomographic device according to claim 4 wherein said imaging condition displayed on said displaying means is a position of said body.

6. A tomographic device according to claim 1 wherein a single imaging means is used as both said first imaging means and said second imaging means.

7. A tomographic device according to claim 1, wherein the detecting means detects light and a tomographic image is obtained from the light.

8. A tomographic device according to claim 1, wherein the detecting means is an image identifier or a flat panel detector.

9. A tomographic device according to claim 1, wherein the radiation source is a X-ray tube for radiating X-rays and the detecting means detects X-rays transmitted through the body.

10. A tomographic device according to claim 1, further comprising:
    a worktop on which the body is mounted, the worktop being disposed horizontally such that tomographic imaging is performed while the body lays horizontally on the worktop.

11. A tomographic device according to claim 1, further comprising:
    a worktop on which the body is disposed, the worktop is provided at an angle from a horizontal position, and the body is supported by the worktop when performing tomographic imaging.

12. A tomographic device according to claim 1, wherein the tomographic imaging device is a C-arm fluoroscopic device.

13. A tomographic device according to claim 1, wherein the tomographic imaging device is a cone-beam CT device.

14. A tomographic device according to claim 1, wherein the tomographic imaging device is a non-C-arm fluoroscopic device, the body is scanned as the radiation source and the detecting means move horizontally in opposite directions while interposing the body, and the preliminary imaging is performed from an axis perpendicular to the direction of the movement of the radiation source or the detecting means.

15. A tomographic device according to claim 1, wherein the tomographic imaging device is a non-C-arm fluoroscopic device, the body is disposed horizontally for scanning, a radiation axis connecting the radiation source and detecting means is tilted at a predetermined angle relative to a plumb axis, and the body is rotationally scanned around the plumb axis.

16. A tomographic device according to claim 1, wherein separate imaging means separately serves as first imaging means and second imaging means.

* * * * *